(12) United States Patent
Cordoliani et al.

(10) Patent No.: US 8,852,633 B2
(45) Date of Patent: Oct. 7, 2014

(54) ORODISPERSIBLE DOMPERIDONE TABLETS

(75) Inventors: Jean-François Cordoliani, Sainte Foy d'Aigrefeuille (FR); Didier Berthoumieu, Villenouvelle (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 857 days.

(21) Appl. No.: 12/224,945

(22) PCT Filed: Mar. 14, 2007

(86) PCT No.: PCT/EP2007/052388
§ 371 (c)(1),
(2), (4) Date: Nov. 7, 2008

(87) PCT Pub. No.: WO2007/104771
PCT Pub. Date: Sep. 20, 2007

(65) Prior Publication Data
US 2009/0081288 A1    Mar. 26, 2009

(30) Foreign Application Priority Data
Mar. 15, 2006   (FR) .................................... 06 02253

(51) Int. Cl.
*A61K 9/20* (2006.01)
*A61K 31/445* (2006.01)
*A61K 31/454* (2006.01)
*A61K 9/00* (2006.01)

(52) U.S. Cl.
CPC ............. *A61K 9/2077* (2013.01); *A61K 9/2018* (2013.01); *A61K 9/2054* (2013.01); *A61K 31/454* (2013.01); *A61K 9/0056* (2013.01)
USPC .......................................... 424/464; 514/322

(58) Field of Classification Search
USPC .......................................... 424/464; 514/322
See application file for complete search history.

(56) References Cited

U.S. PATENT DOCUMENTS

| 6,475,510 | B1 | 11/2002 | Venkatesh et al. |
| 8,071,128 | B2 | 12/2011 | Ohta et al. |
| 2001/0014340 | A1* | 8/2001 | Ohta et al. ............... 424/400 |
| 2002/0061932 | A1* | 5/2002 | Gimona et al. .......... 514/567 |
| 2003/0118642 | A1* | 6/2003 | Norman et al. .......... 424/465 |
| 2007/0218129 | A1 | 9/2007 | Besse |

FOREIGN PATENT DOCUMENTS

| FR | 2 858 556 A1 | 2/2005 |
| FR | 2 858 556 A1 | 2/2005 |
| KR | 10-2001-0006835 A | 1/2006 |
| WO | WO 00/57857 A1 | 10/2000 |
| WO | WO-03/061584 A1 | 7/2003 |

OTHER PUBLICATIONS

Brittain (Analytical Profiles of Drug Substances and Excipients, vol. 24, pp. 310, 311, and 314).*

* cited by examiner

*Primary Examiner* — Adam C Milligan
(74) *Attorney, Agent, or Firm* — Birch, Stewart, Kolasch & Birch, LLP

(57) ABSTRACT

The present invention relates to an orodispersible tablet comprised of, by weight: a maximum of 15% of a low-dose, therapeutically active substance; from 55% to 70% of mannitol of a particle size between 30 μm and 300 μm; at least 2% of maltodextrin; from 3.5% to 8% of croscarmellose sodium; from 10% to 20% of microcrystalline cellulose; from 0.5% to 1.5% of magnesium stearate; and from 1% to 5% of flavoring (s) and sweetener (s).

19 Claims, No Drawings

ORODISPERSIBLE DOMPERIDONE TABLETS

The present invention relates to a novel solid composition of a low-dose, therapeutically active substance in the form of an orodispersible tablet which quickly disintegrates in the oral cavity while having low friability and suitable hardness, and which can be manufactured under good industrial conditions.

Within the framework of the present patent application, a "low-dose, therapeutically active substance" means an active substance present within a tablet in an amount that is at most 15%, preferably from 0.5% to 12%, by weight compared to the total weight of the tablet. Among the active ingredients more particularly targeted by the present invention, domperidone, mequitazine, codeine base and loperamide hydrochloride can be cited as illustrative examples. However, the invention is not limited to these specific active ingredients, but extends rather to all therapeutic active ingredients generally administered at low doses.

In particular, domperidone is traditionally administered to relieve symptoms of nausea and vomiting among patients who, notably due to a tendency toward gastric regurgitation, have particular difficulty swallowing traditional solid tablets which, moreover, must be taken with an additional quantity of water. This problem is particularly acute with infants and the elderly, who preferably have the option of taking oral suspensions of domperidone. However, this particular mode of administration poses other problems, in particular with respect to dosages that require the use of graduated syringes, which are always difficult to use, especially to administer low doses of domperidone, for example 10 mg unit doses.

Orodispersible compositions that disintegrate more or less quickly in the oral cavity, but that often pose significant problems because of high friability and low hardness, are of course already known. Such tablets require the use of aluminum blister packaging which effectively protects the tablets during storage but which necessarily causes the tablet to break during its removal from the blister package. In addition, other difficulties can emerge during the manufacture of such tablets, in particular due to problems related to the flow of the powdery mixtures used to form more or less spherical granules. Indeed, the latter can exhibit large variations in shape and weight, notably due to agglomeration phenomena that can appear in the various mixing stages of powdery materials.

After taking into account and varying a very large number of parameters during the development of the tablet of the invention, such as the nature of the excipients, the compatibility of same as well as specific manufacturing conditions, the applicant has developed a composition endowed with all of the properties sought and which, moreover, is easy to produce industrially. Lastly, an additional advantage lies in the fact that the present invention makes it possible to formulate uncoated active ingredients.

In accordance with the present invention, the orodispersible tablet is comprised of, by weight:
- a maximum of 15% of a low-dose, therapeutically active substance;
- from 55% to 70% of mannitol of a particle size between 30 µm and 300 µm;
- at least 2% of maltodextrin;
- from 3.5% to 8% of croscarmellose sodium;
- from 10% to 20% of microcrystalline cellulose;
- from 0.5% to 1.5% of magnesium stearate; and
- from 1% to 5% of flavoring(s) and sweetener(s).

According to another characteristic of the present invention, the orodispersible tablet is comprised of, by weight:
- from 0.5% to 12% of a low-dose, therapeutically active substance;
- from 55% to 70% of mannitol of a particle size between 30 µm and 300 µm;
- at least 2% of maltodextrin;
- from 3.5% to 8% of croscarmellose sodium;
- from 10% to 20% of microcrystalline cellulose;
- from 0.5% to 1.5% of magnesium stearate; and
- from 1% to 5% of flavoring(s) and sweetener(s).

According to another characteristic of the present invention, the orodispersible tablet is comprised of, by weight:
- from 0.5% to 12% of a low-dose, therapeutically active substance selected among domperidone, mequitazine, codeine base and loperamide hydrochloride;
- from 55% to 70% of mannitol of a particle size between 30 µm and 300 µm;
- at least 2% of maltodextrin;
- from 3.5% to 8% of croscarmellose sodium;
- from 10% to 20% of microcrystalline cellulose;
- from 0.5% to 1.5% of magnesium stearate; and
- from 1% to 5% of flavoring(s) and sweetener(s).

According to another characteristic of the present invention, the orodispersible tablet is comprised of, by weight:
- from 0.5% to 12% of domperidone;
- from 55% to 70% of mannitol of a particle size between 30 µm and 300 µm;
- at least 2% of maltodextrin;
- from 3.5% to 8% of croscarmellose sodium;
- from 10% to 20% of microcrystalline cellulose;
- from 0.5% to 1.5% of magnesium stearate; and
- from 1% to 5% of flavoring(s) and sweetener(s).

Among the large number of binding agents a priori useful in these types of orodispersible tablets, whose total unit weight can vary from 50 mg to 600 mg, the applicant has chosen to use maltodextrin, which, when used in a proportion of 1% by weight, exhibits cleavage problems during tableting that disappear at values greater than or equal to approximately 2% by weight of maltodextrin compared to the total weight of the orodispersible tablet.

In an advantageous fashion, the maltodextrin used has a maximum dextrose equivalent (DE) value of 15. In practice, the maltodextrin used will advantageously have an average particle size of approximately 100 µm.

Among the binding agents a priori conceivable for use in the production of such tablets, hydroxypropyl methylcellulose, polyvidone K30, gum arabic and saccharose can be cited. Among the aforementioned binding agents, none has a disintegration time of less than 30 seconds with the exception of saccharose, which, however, must be ruled out because this binding agent, in addition to its cariogenic character, is too sensitive to ambient moisture.

During the development of the formulation, it was also necessary to choose a disaggregating agent. Among a priori conceivable disaggregating agents, corn starch, crospovidone and croscarmellose calcium can be cited. These three disaggregating agents, however, do not make it possible to achieve a suitable disintegration time; corn starch, in addition, leads to problems of significant cleavage or high friability with the tablets obtained. The disaggregating agent that proved to yield the best results was croscarmellose sodium. Its use in a proportion of 3.5% to 8% by weight indeed led to satisfactory disintegration times. Thus, by using croscarmellose in a proportion of 7% by weight, it was observed that the tablet disintegrated in the oral cavity after approximately 20 seconds.

Given that the orodispersible tablet according to the invention is obtained after the tableting of a combination of an internal phase necessarily comprised of the low-dose, therapeutically active substance, mannitol and maltodextrin, and an external phase with the additional excipients of the tablet, it proved desirable to distribute the croscarmellose sodium partially in the internal phase and to incorporate the remainder in the external phase. In practice, the best results relative to disintegration time were obtained by distributing approximately half of the total quantity of sodium croscarmellose in the internal phase and approximately half in the external phase of the tablet. By distributing the croscarmellose sodium between the internal and external phases in such a way, a disintegration time of approximately 20 seconds is indeed obtained, whereas weight distributions between the two phases of 25/75 or 75/25 lead to disintegration times at least twice as high.

The specific choice of diluent used is also essential for obtaining good properties of hardness and dispersibility. The a priori conceivable diluents that were tested include lactose, sorbitol and microcrystalline cellulose. In standard incorporation proportions, all the aforementioned diluents lead to disintegration times that are far too high, except for cellulose, whose disadvantage relates to its undesirable gustatory perception. In addition, if microcrystalline cellulose is used in too great a proportion, production problems then arise with conventional tablet machines. This is why only mannitol was deemed suitable as a diluent. The use of mannitol, with a preferential mean particle size of approximately 160 µm, in a proportion ranging between approximately 55% and 70% by weight of the total tablet, leads to good mechanical properties for the tablet. Indeed, it was determined that by using said mannitol in said proportions all problems of tablet cleavage and high friability were avoided.

Notable among excipients for use in the external phase is microcrystalline cellulose, which must be used advantageously in a proportion of 10% to 20% by weight. Indeed, the use of quantities greater than approximately 20% disturbs the rheological properties of the mixture to be tableted. On the other hand, the use of lower quantities, in particular quantities lower than 10%, lead to cleavage problems with the final tablet.

In accordance with a particularly advantageous embodiment of the present invention, the orodispersible tablet has the following centesimal formula:

|  |  |
| --- | --- |
| domperidone | 6% |
| mannitol 60 | 65% |
| maltodextrin | 5% |
| sodium croscarmellose | 5% |
| microcrystalline cellulose | 15% |
| acesulfame potassium | 1% |
| flavoring | 1% |
| ammonium glycyrrhizate | 1% |
| magnesium stearate | 1% |

The present invention also relates to a method for manufacturing the orodispersible tablets described above. One such method is characterized by the implementation of the following successive steps:

a) dry mixing the low-dose, therapeutically active substance, mannitol, maltodextrin and a portion, preferably approximately half, of the croscarmellose sodium;

b) adding water to the mixture thus obtained and compounding;

c) comminuting the wet mass obtained in step b) using an oscillating granulator;

d) fluid-bed drying the granules obtained in step c);

e) sizing the granules and a portion of the external phase using an oscillating granulator;

f) adding a portion of the external-phase excipients partially or entirely during the drying and/or sizing phase;

g) final mixing of all of the materials comprising the formula, and h) tableting said components.

In particular, half of the croscarmellose sodium is introduced into the internal phase and the other half is introduced into the external phase.

According to one characteristic of the method, dry mixing step a) is carried out in a barrel-type or blade mixer.

According to another characteristic of the method, step b) consists of adding purified water, followed by compounding.

According to another characteristic of the method, step c), comminuting using an oscillating granulator, is carried out using an 8 mm screen.

According to another characteristic of the method, another portion of the external phase is added at the end of step d) and before step e) of sizing using an oscillating granulator.

According to another characteristic of the method, a portion of the external phase is added after step e) of sizing using an oscillating granulator.

Lastly, after the final mixing step that leads to lubricated granules, the residual moisture content will be monitored and maintained at a value of less than or equal to 3%.

The present invention will be described below in more detail by specifying the manufacturing process of the orodispersible domperidone tablets according to the invention. This method involves several steps, as indicated in the examples.

EXAMPLE 1

Domperidone Tablet

Step 1:
In a planetary or blade mixer, introduce the following compounds:
mannitol 60
domperidone
maltodextrin
croscarmellose sodium (50% of the total quantity)
Mix
Step 2:
In a receptacle of sufficient capacity, introduce:
purified water
Slowly pour the purified water on the moving mixture.
Mix until a mass suitable for granulation is obtained.
Step 3:
Comminute the wet mass obtained in step 2 using an oscillating granulator equipped with an 8 mm screen.
Collect the comminuted granules in a tared fluid bed tank.
Step 4:
Dry the wet granules in a fluid bed until the residual moisture content is less than or equal to 2%.
Step 5:
Size the following using an oscillating granulator equipped with a 1 mm screen:
the dried granules
mint flavor
acesulfame potassium
ammonium glycyrrhizate
vegetable magnesium stearate
Recover all of the material in a container and then incorporate:
sodium croscarmellose (50% of the total quantity)
microcrystalline cellulose Step 6:
Mix the final mixture obtained in step 5 using a reversing mixer.

Step 7:
Tablet the lubricated granules on a punch-and-die rotary press.

Evaluate the following technical characteristics:
mean weight and weight uniformity
tablet thickness
friability: <0.2%
disintegration time in 37° C. water: less than 1 min
crushing strength: 20-30 N on average
unit weight: 170 mg Such tablets in conformity with the present invention exhibit:
friability of less than 0.2%,
disintegration time in 37° C. water of less than 1 min,
crushing strength of 20 to 30 newtons.

By implementing an orodispersible domperidone tablet manufacturing process such as described above, tablets exhibiting the desired hardness properties can also be obtained.

EXAMPLE 2

Tablet Containing Mequitazine

EXAMPLE 3

Tablet Containing Codeine Base

EXAMPLE 4

Tablet containing Loperamide HCl

|  | EXAMPLE 2 MEQUITAZINE 10 mg | EXAMPLE 3 CODEINE BASE 18.83 mg | EXAMPLE 4 LOPERAMIDE HCl 2 mg |
|---|---|---|---|
| Mannitol | 110.2 mg | 101.32 mg | 118.2 mg |
| Maltodextrin | 5.0 mg | 4.4 mg | 6.4 mg |
| Sodium croscarmellose | 12 mg | 12 mg | 12 mg |
| Microcrystalline cellulose | 18.4 mg | 21 mg | 17 mg |
| Mint flavor | 4.5 mg | 4.5 mg | 4.5 mg |
| Acesulfame potassium | 3 mg | 3 mg | 3 mg |
| Ammonium glycyrrhizate | 0.5 mg | 0.5 mg | 0.5 mg |
| Vegetable magnesium stearate | 1.4 mg | 1.4 mg | 1.4 mg |
| Purified water | Q.S. | Q.S. | Q.S. |
| Mean hardness (N) | 23 N | 30 N | 34 N |
| Mean disintegration time (sec) | 20 sec | 30 sec | 40 sec |
| Friability (%) 100 turns | 0.14% | 0.06% | 0.05% |

The invention claimed is:

1. An orodispersible tablet comprised of, by weight:
   a maximum of 15% of a low-dose, therapeutically active substance;
   from 55% to 70% of mannitol of a particle size between 30 μm and 300 μm;
   at least 2% of maltodextrin;
   from 3.5% to 8% of croscarmellose sodium;
   from 10% to 20% of microcrystalline cellulose;
   from 0.5% to 1.5% of magnesium stearate; and
   from 1% to 5% of flavoring (s) and sweetener (s);
   wherein the tablet comprises a combination of an internal phase containing the therapeutic active substance and an initial portion of croscarmellose sodium, and an external phase containing a second portion of croscarmellose sodium; and
   wherein approximately half of the total quantity of sodium croscarmellose is distributed in the internal phase and approximately half is distributed in the external phase of the tablet.

2. An orodispersible tablet according to claim 1, wherein said tablet is comprised of, by weight:
   from 0.5% to 12% of a low-dose, therapeutically active substance;
   from 55% to 70% of mannitol of a particle size between 30 μm and 300 μm;
   at least 2% of maltodextrin;
   from 3.5% to 8% of croscarmellose sodium;
   from 10% to 20% of microcrystalline cellulose;
   from 0.5% to 1.5% of magnesium stearate; and
   from 1% to 5% of flavoring (s) and sweetener (s).

3. An orodispersible tablet according to claim 1, wherein said tablet is comprised of, by weight:
   from 0.5% to 12% of a low-dose, therapeutically active substance selected among domperidone, mequitazine, codeine base and loperamide hydrochloride;
   from 55% to 70% of mannitol of a particle size between 30 μm and 300 μm;
   at least 2% of maltodextrin;
   from 3.5% to 8% of croscarmellose sodium;
   from 10% to 20% of microcrystalline cellulose;
   from 0.5% to 1.5% of magnesium stearate; and
   from 1% to 5% of flavoring (s) and sweetener (s).

4. An orodispersible tablet according to claim 1, wherein said tablet is comprised of, by weight:
   from 0.5% to 12% of domperidone;
   from 55% to 70% of mannitol of a particle size between 30 μm and 300 μm;
   at least 2% of maltodextrin;
   from 3.5% to 8% of croscarmellose sodium;
   from 10% to 20% of microcrystalline cellulose;
   from 0.5% to 1.5% of magnesium stearate; and
   from 1% to 5% of flavoring (s) and sweetener (s).

5. An orodispersible tablet according to claim 1, wherein it is provided as a combination of an internal phase containing domperidone, mannitol, maltodextrin and an initial portion of croscarmellose sodium, and an external phase containing a second portion of croscarmellose sodium, microcrystalline cellulose, magnesium stearate as well as flavors and sweeteners.

6. An orodispersible tablet according to claim 1, wherein the maltodextrin has a maximum dextrose equivalent (DE) value of 15.

7. An orodispersible tablet according to claim 1, wherein the maltodextrin has a mean particle size of approximately 100 μm.

8. An orodispersible tablet according to claim 5, wherein the internal phase of the tablet consists of dry granules having a residual moisture content of less than or equal to 2%.

9. An orodispersible tablet according to claim 1, characterized by the following centesimal formula:

| | |
|---|---|
| domperidone | 6% |
| mannitol 60 | 65% |
| maltodextrin | 5% |
| sodium croscarmellose | 5% |
| microcrystalline cellulose | 15% |
| acesulfame potassium | 1% |
| flavoring | 1% |
| ammonium glycyrrhizate | 1% |
| magnesium stearate | 1%. |

10. An orodispersible tablet according to claim 1, wherein said tablet exhibits:

| |
|---|
| friability of less than 0.2%, |
| disintegration time in 37° C. water of less than 1 min, |
| crushing strength of 20 to 30 newtons. |

11. A method for manufacturing the tablets according to claim 1, characterized by the implementation of the following successive steps:
a) dry mixing the low-dose, therapeutically active substance, mannitol, maltodextrin and a portion, preferably approximately half, of the croscarmellose sodium;
b) adding water to the mixture thus obtained and compounding;
c) comminuting the wet mass obtained in step b) using an oscillating granulator;
d) fluid-bed drying the granules obtained in step c);
e) sizing the granules and a portion of the external phase using an oscillating granulator;
f) adding a portion of the external-phase excipients partially or entirely during the drying and/or sizing phase;
g) tableting said components.

12. A method according to claim 11, wherein half of the croscarmellose sodium is introduced during the dry mixing of the internal-phase excipients and the other half of the croscarmellose sodium is introduced during the addition of the external-phase excipients.

13. A method according to claim 11, wherein dry mixing a) is carried out in a planetary or blade mixer.

14. A method according to claim 11, wherein step b) consists of adding purified water, followed by compounding.

15. A method according to claim 11, wherein step c), comminuting using an oscillating granulator, is carried out using an 8 mm screen.

16. A method according to claim 11, wherein the drying step d) is carried out in a fluid bed.

17. A method according to claim 11, wherein mint flavor, acesulfame potassium, ammonium glycyrrhizate and magnesium stearate are added to the granules at the end of the fluid-bed drying step d).

18. A method according to claim 11, wherein the croscarmellose sodium and the microcrystalline cellulose are added after step e) of sizing using an oscillating granulator equipped with a 1 mm screen.

19. An orodispersible tablet according to claim 2, wherein said tablet is comprised of, by weight:
from 0.5% to 12% of a low-dose, therapeutically active substance selected among domperidone, mequitazine, codeine base and loperamide hydrochloride;
from 55% to 70% of mannitol of a particle size between 30 μm and 300 μm;
at least 2% of maltodextrin;
from 3.5% to 8% of croscarmellose sodium;
from 10% to 20% of microcrystalline cellulose;
from 0.5% to 1.5% of magnesium stearate; and
from 1% to 5% of flavoring (s) and sweetener (s).

* * * * *